(12) United States Patent
Andersson et al.

(10) Patent No.: US 8,913,770 B2
(45) Date of Patent: Dec. 16, 2014

(54) TRANSCUTANEOUS BONE CONDUCTION SYSTEM

(75) Inventors: Marcus Andersson, Goteborg (SE); Patrick Wilhelm Strömsten, Molnlycke (SE)

(73) Assignee: Cochlear Limited, Macquarie University, NSW (AU)

( * ) Notice: Subject to any disclaimer, the term of this patent is extended or adjusted under 35 U.S.C. 154(b) by 313 days.

(21) Appl. No.: 13/260,529

(22) PCT Filed: Mar. 25, 2010

(86) PCT No.: PCT/US2010/028744
§ 371 (c)(1),
(2), (4) Date: Dec. 27, 2011

(87) PCT Pub. No.: WO2010/111547
PCT Pub. Date: Sep. 30, 2010

(65) Prior Publication Data
US 2012/0095283 A1    Apr. 19, 2012

(30) Foreign Application Priority Data
Mar. 25, 2009  (DE) .......................... 10 2009 014 772

(51) Int. Cl.
*H04R 25/00*    (2006.01)
(52) U.S. Cl.
CPC .......... *H04R 25/606* (2013.01); *H04R 2460/13* (2013.01)
USPC ............................. 381/326; 381/380; 181/129
(58) Field of Classification Search
USPC ............ 381/312, 326, 380, 313–321; 600/25; 181/129, 130, 135
See application file for complete search history.

(56) References Cited

U.S. PATENT DOCUMENTS

| | | |
|---|---|---|
| 4,498,461 A | 2/1985 | Hakansson |
| 5,346,492 A | 9/1994 | Morgan |
| 6,032,677 A | 3/2000 | Blechman et al. |
| 7,065,223 B2 | 6/2006 | Westerkull |
| 8,254,610 B2 | 8/2012 | Heerlein et al. |
| 2002/0143268 A1 | 10/2002 | Meredith et al. |
| 2004/0116772 A1* | 6/2004 | Lupin et al. ..................... 600/25 |
| 2006/0058819 A1* | 3/2006 | Kasic et al. ................... 606/151 |
| 2007/0053536 A1* | 3/2007 | Westerkull ..................... 381/326 |
| 2007/0270684 A1 | 11/2007 | Cawley et al. |
| 2011/0183291 A1 | 7/2011 | Malo Carvalho et al. |
| 2012/0040301 A1 | 2/2012 | Ngiam |

OTHER PUBLICATIONS

International Search Report; International Application No. PCT/US2010/028744 mailed May 20, 2010 (2 pages).
Written Opinion; International Application No. PCT/US2010/028744 mailed May 20, 2010 (5 pages).

* cited by examiner

*Primary Examiner* — Curtis Kuntz
*Assistant Examiner* — Sunita Joshi
(74) *Attorney, Agent, or Firm* — Lowe Hauptman & Ham, LLP

(57) ABSTRACT

A transcutaneous bone conduction system comprising a bone conduction device configured to vibrate in response to received sound. The system also comprises a totally implantable support apparatus positionable under a recipient's skin, comprising: a fixture configured to be implanted in the skull, and a substantially rigid cradle. The cradle has opposing, spaced plates connected by a bridge member, wherein a first of the plates is configured to be secured to the fixture and wherein the space between the plates is sufficient to receive the bone conduction device, and wherein the plates are configured to retain the bone conduction device against the skin proximate to the first plate.

29 Claims, 8 Drawing Sheets

TRANSCUTANEOUS BONE CONDUCTION SYSTEM

CROSS-REFERENCE TO RELATED APPLICATIONS

This application is a national stage application of PCT Application No. PCT/US2010/028744, entitled, "Transcutaneous Bone Conduction System," filed on Mar. 25, 2010, which claims foreign priority to German Patent Application No. No. 102009014772.1, "Hearing Aid Device," filed on 25 Mar. 2009, the contents of these applications being incorporated by reference herein.

BACKGROUND

1. Field of the Invention

The present invention relates generally to hearing prostheses and, more particularly, to a transcutaneous bone conduction system.

2. Related Art

For persons who cannot benefit from traditional acoustic hearing aids, there are other types of commercially available hearing prostheses such as, for example, bone conduction hearing prostheses (also referred to as "bone conduction hearing aids," and "bone conduction devices;" "bone conduction devices" herein). Bone conduction devices mechanically transmit sound information to a person's inner ear by transferring vibrations to person's skull. This enables the hearing prosthesis to be effective regardless of whether there is disease or damage in the middle ear.

Traditionally, bone conduction devices transfer vibrations from an external vibrator to the skull through a bone fixture that penetrates the skin and is physically attached to both the vibrator and the skull. Typically, the external vibrator is connected to the percutaneous bone fixture located behind the external ear so that sound is transmitted via the skull to the cochlea.

SUMMARY

In one aspect of the present invention, a transcutaneous bone conduction system is provided. The system comprises: a bone conduction device configured to vibrate in response to received sound; a totally implantable support apparatus positionable under a recipient's skin, comprising: a fixture configured to be implanted in the skull; and a substantially rigid cradle having first and second opposing, spaced plates connected by an bridge member, wherein the first plate is configured to be secured to the fixture and wherein the space between the plates is sufficient to receive the bone conduction device, and wherein the plates are configured to retain the bone conduction device against the skin proximate to the first plate.

In another aspect of the present invention, a totally implantable support apparatus positionable under a recipient's skin configured for use with a bone conduction device that vibrates in response to received sound. The apparatus comprises: a fixture configured to be implanted in the skull; and a substantially rigid cradle having opposing, spaced plates connected by an bridge member, wherein a first of the plates is configured to be secured to the fixture and wherein the space between the plates is sufficient to receive the bone conduction device, and wherein the plates are configured to retain the bone conduction device against the skin proximate to the first plate.

BRIEF DESCRIPTION OF THE DRAWINGS

Embodiments of the present invention are described below with reference to the attached drawing in which.

DETAILED DESCRIPTION

Aspects of the present invention are generally directed to a transcutaneous bone conduction system. In one embodiment, the transcutaneous bone conduction system comprises a totally implantable support apparatus configured to support, through a layer of skin of the recipient, a bone conduction device in the form of a Behind-The-Ear (BTE) unit. The totally implantable support apparatus comprises a substantially rigid cradle having first and second opposing and spaced plates which are connected by a bridge member. The first plate is configured to be secured to the fixture, and the space between the plates is sufficient to receive the bone conduction device therein. The plates are configured to retain the bone conduction device against the skin proximate to the first plate.

Figure 1:
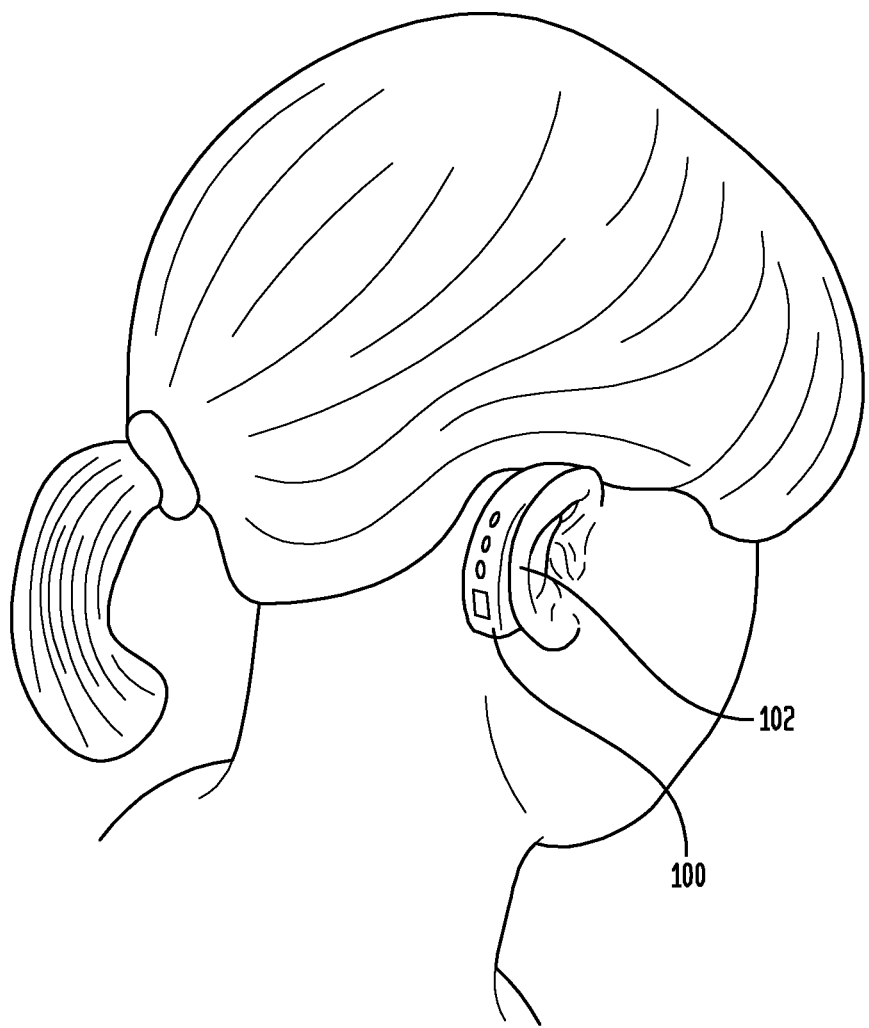
FIG. 1 is a perspective view of a recipient illustrating an exemplary external location of a behind-the-ear (BTE) unit of a bone conduction system, in accordance with embodiments of the present invention.
Figure 2:
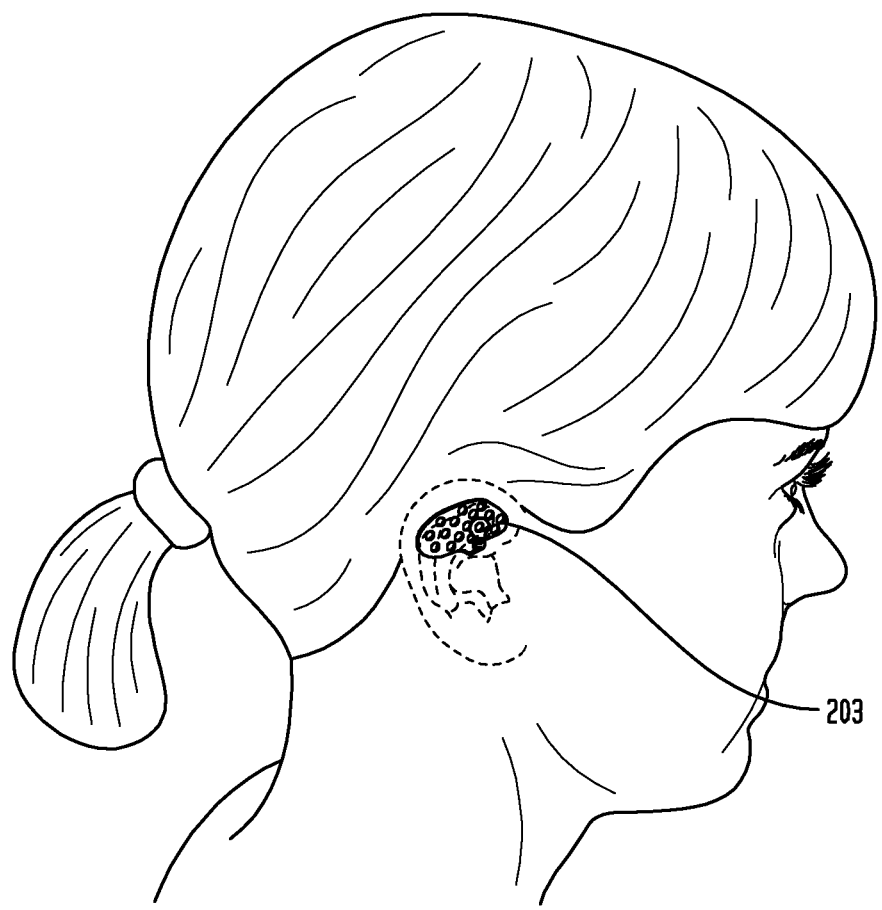
FIG. 2 is a perspective and partially sectional view of a patient illustrating the location of an implanted support apparatus relative to the ear of a recipient in accordance with embodiments of the present invention.

FIGS. 1 and 2 illustrate a transcutaneous bone conduction system in accordance with embodiments of the present invention. As shown in FIG. 1, the system comprises a BTE bone conduction device 100 positioned behind the outer ear 102 of a recipient. Bone conduction device 100 comprises a vibrator configured to generate mechanical forces based on a received sound signal. The mechanical forces, when transferred to the recipient's skull, cause a hearing perception of the received sound signal. Bone conduction devices are known in the art and will not be further described herein.

The illustrative bone conduction system of FIGS. 1 and 2 further includes a totally implantable support apparatus 203 which, as described in detail below, is configured to support bone conduction device 100. FIG. 2 illustrates an exemplary location for support apparatus 203. The details of exemplary locations for support apparatus 203 are also described in further detail below.

Figure 3:
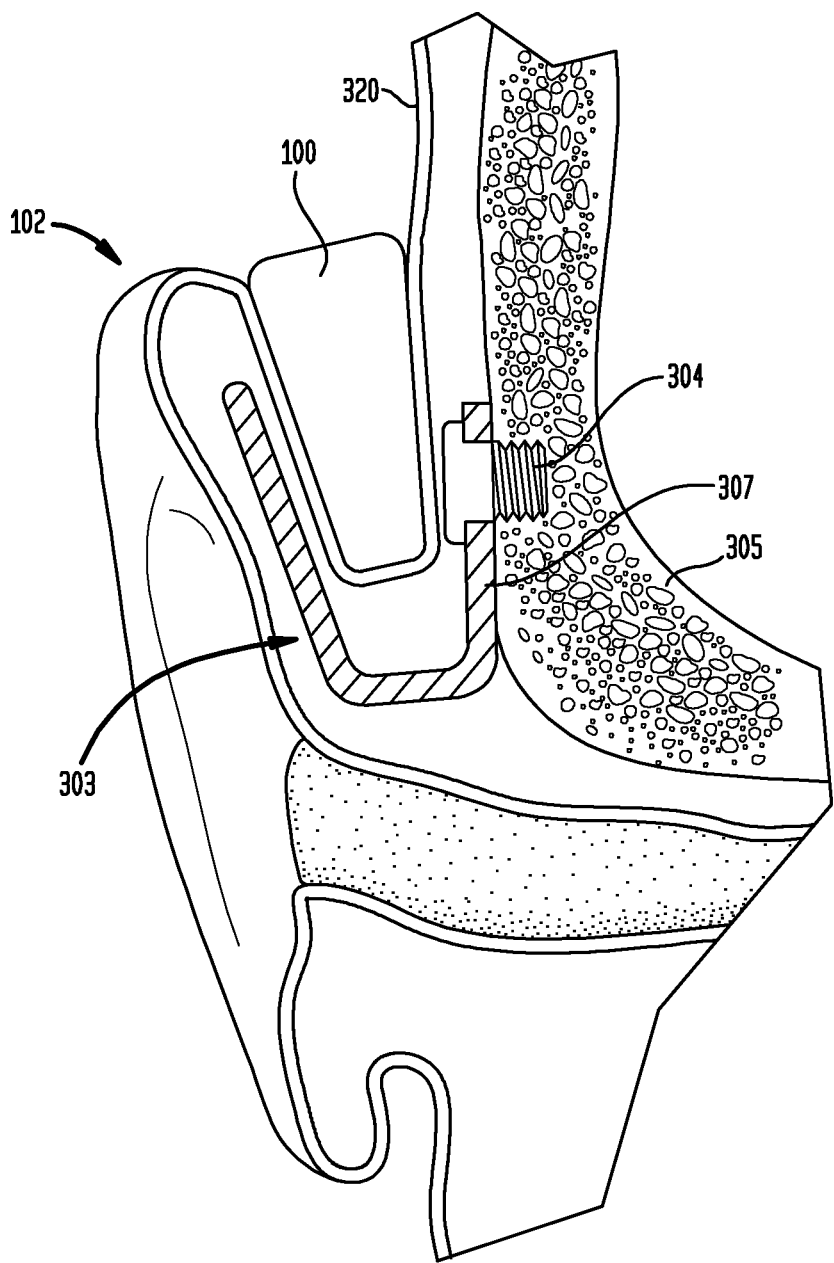
FIG. 3 is a partially cross-sectional view of an implanted support apparatus in accordance with embodiments of the present invention.

FIG. 3 illustrates an embodiment of a bone conduction system in accordance with embodiments of the present invention comprising bone conduction device 100, and an exemplary totally implantable support apparatus 303. Support apparatus 303 comprises a substantially rigid cradle 307 implantable under the recipient's skin 320. As shown, a portion of cradle 307 is contoured to follow the anatomy of the recipient's skull 305, while another portion is configured to be positioned in the recipient's outer ear 102. In the illustrative arrangement of FIG. 3, cradle 307 is partially implanted in the recipient's pinna 102. As shown, support apparatus 303 supports bone conduction device 100 through the skin 320. Implantable support apparatus 303, according to the embodiment of FIG. 3, comprises a threaded bone fixture 304 for anchoring cradle 307 to the recipient's skull 305. In the embodiment depicted in FIG. 3, support apparatus 303 is located above the outer ear 102, and cradle 307 forms a generally U-shape, where the interior of the U-shape cradles bone conduction device 100 so that the bone conduction device is retained against the skin 320 adjacent the skull 305 above and/or behind the outer ear 102. In an embodiment, fixture 304 is placed at a location proximate a location just above the junction of the upper part of the outer ear (the pinna) and the skull 305.

In embodiments of the present invention, vibrations representative of sound received by the bone conduction system are produced by bone conduction device 100 while bone conduction device 100 is held in place by the support apparatus 303. The vibrations representative of received sound are transmitted through the outer skin layer 320 and ultimately to the skull 305 (for conduction to the cochlea). More specific features of some embodiments will now be described.

Bone conduction device 100 in the embodiment just described is completely external to the body of the recipient. That is, no part of bone conduction device 100 penetrates the outer skin layer 320 of the recipient. Bone conduction device 100 is thus not directly attached to the support apparatus 303 anchored to the skull 305. As noted above, in an embodiment, bone conduction device 100 includes a vibrator configured to generate vibrations corresponding to sound received by the transcutaneous bone conduction system.

In some embodiments, bone conduction device 100 includes a sound input element such as a microphone and a sound processor used to convert sound received by the microphone into electrical control signals. These electrical control signals are in-turn used to control the vibrator of bone conduction device 100. In certain embodiments, the microphone and/or the sound processor and/or other control circuitry are separate from bone conduction device 100. For example, the microphone may be located in an in-the-ear component not physically connected to bone conduction device 100, and which communicates with bone conduction device 100 via RF communication. Additionally, the sound processor may be located in a device configured to be attached to a belt, and which communicates with bone conduction device 100 via an extended cable, via RF communication, etc. Any device, system or method that will permit bone conduction device 100 to output vibration that can be transmitted through the skin 320 and associated tissue of a recipient to permit bone conduction hearing assistance may be used in some embodiments. In an embodiment, bone conduction device 100 is a vibrator BTE unit. The size and shape of bone conduction device 100 may be similar to that of a BTE unit of an acoustic hearing aid or of a cochlear implant system, etc.

In an embodiment, support apparatus 303 is anchored to the skull 305 by way of a bone fixture 304 (also referred to herein as a "fixture"). Fixture 304 has threads on a distal end of the bone fixture 304. In some embodiments, the threads are self-tapping threads. An exemplary embodiment utilizes a bone fixture having the functionality and/or associated characteristics, including structure and configuration, of the bone fixtures described in U.S. Pat. No. 4,498,461 and/or U.S. Patent Application Publication No. 2009/0082817, the contents of these documents being incorporated by reference herein for application to configuring fixture 304 for use with support apparatus 303.

Figure 5:
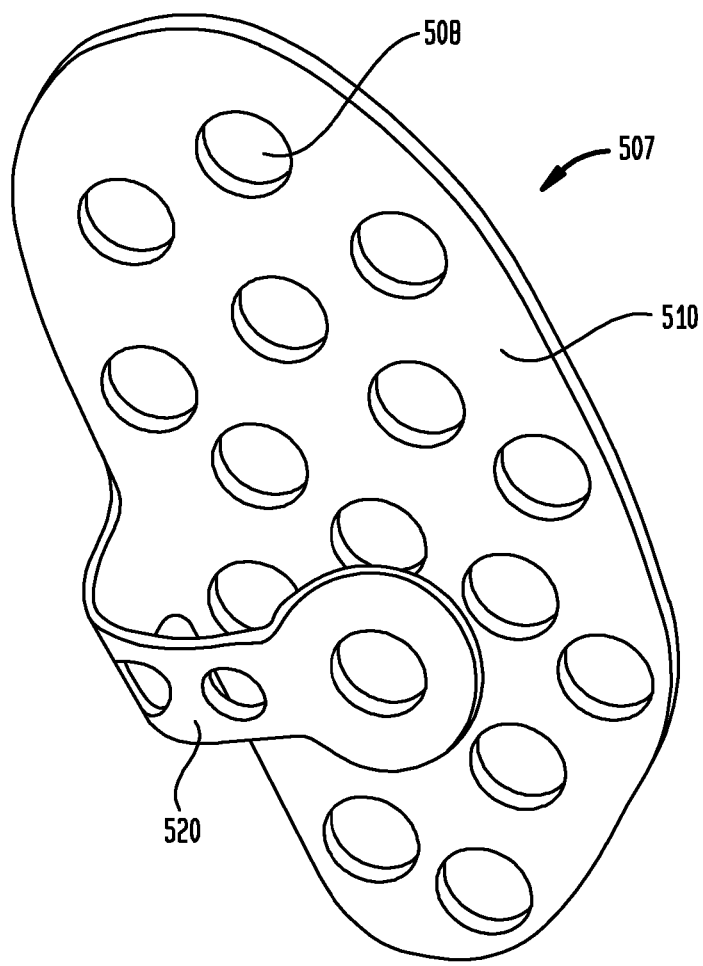
FIG. 5 is a perspective view of an implantable cradle in accordance with embodiments of the present invention.
Figure 6:
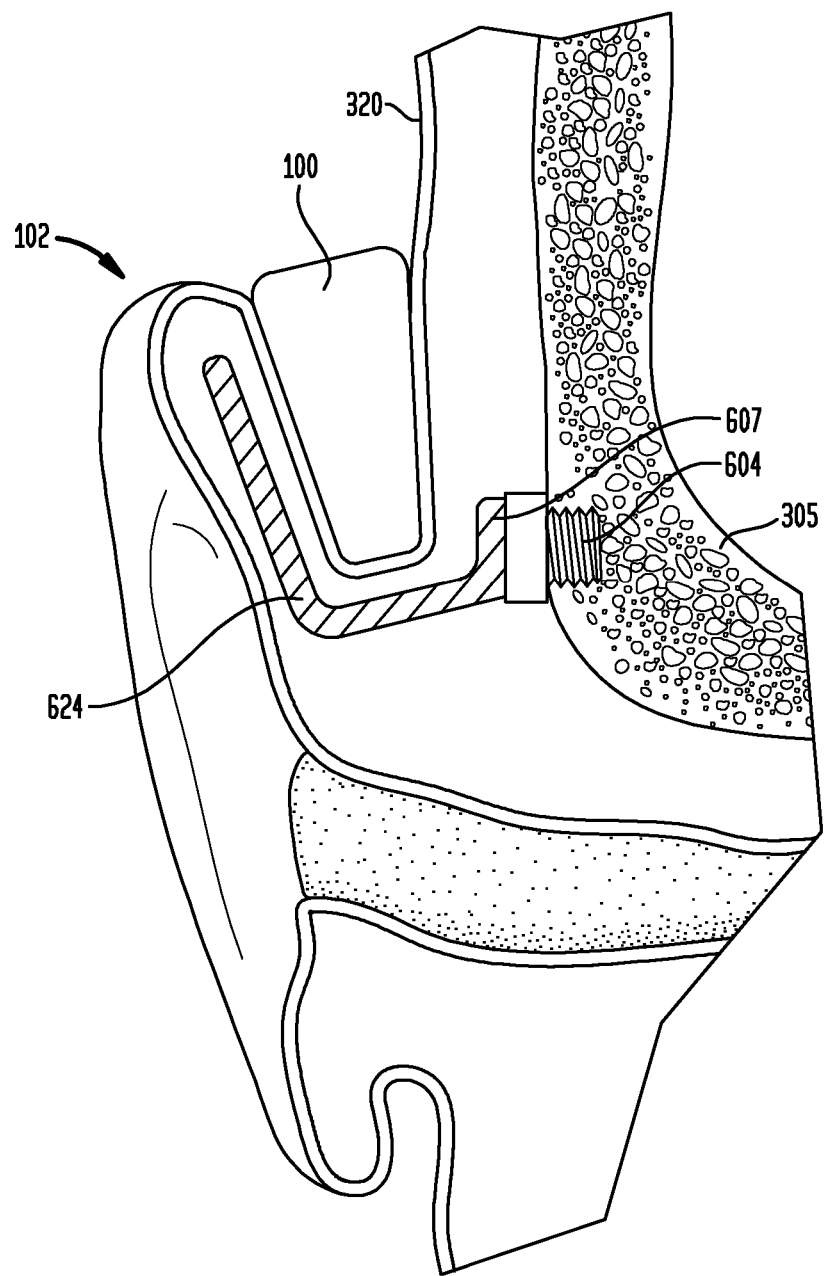
FIG. 6 is a partially cross-sectional view of an implanted support apparatus in accordance with embodiments of the present invention.

By way of example only and not by way of limitation, bone fixture 304 may be directly attached to cradles, as is depicted, for example, in FIGS. 3 and 6. In an embodiment, bone fixture 304 may be inserted through one of the orifices 508 (see FIG. 5, depicting a cradle 507) of the cradle, such as is the case in FIG. 3. Alternatively or in addition, a separate screw or other connecting device (not shown) may be inserted through the cradle, the screw connecting the cradle to the bone fixture. Referring to FIG. 3, in some embodiments, the bone fixture 304/screw attached to the bone fixture 304 is proud of an interior surface of cradle 307 (such as is the case in FIG. 3), or is flush or below the surface of the interior surface of the cradle (see, e.g., screw 422 of FIG. 4B, conveying the same concept but with application to an abutment 406, described in greater detail below).

Figure 4A:
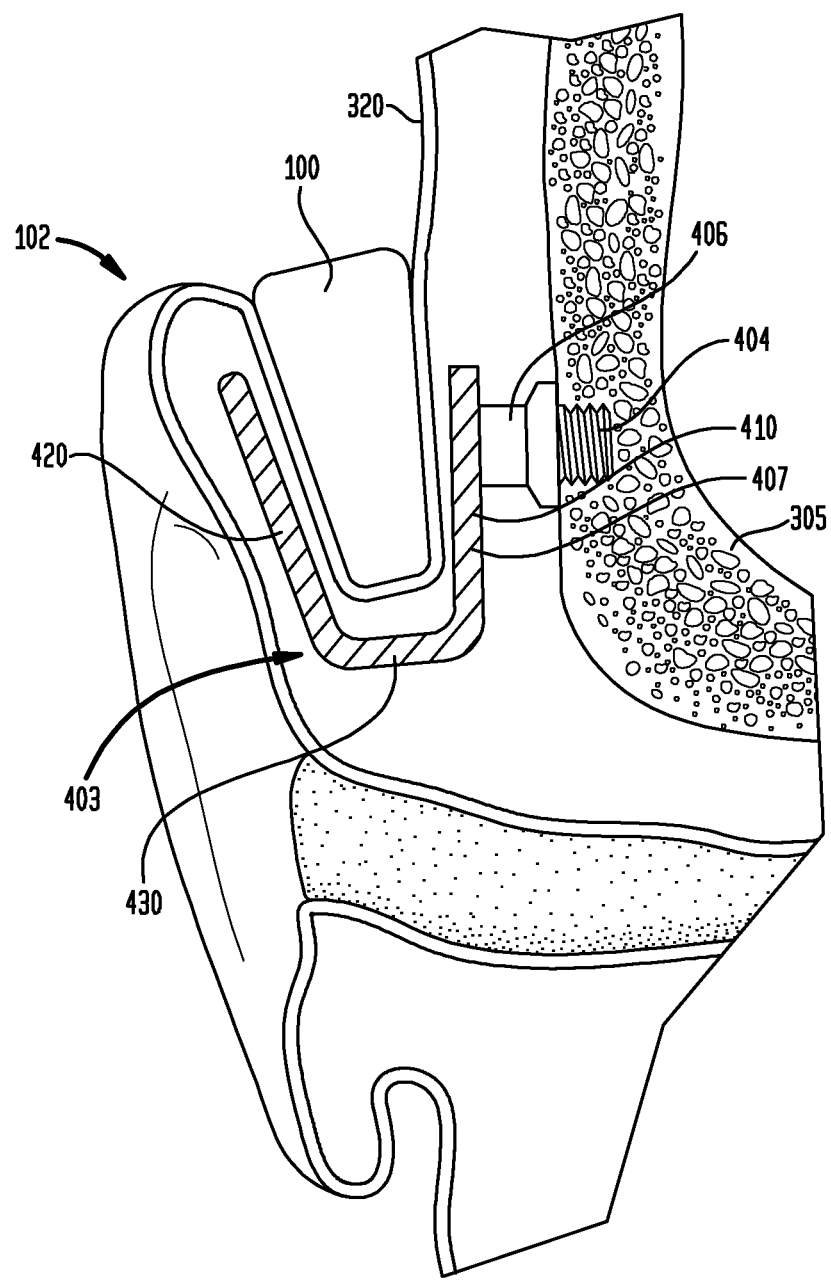
FIG. 4A is a partially cross-sectional view of an implanted support apparatus in accordance with embodiments of the present invention.
Figure 4B:
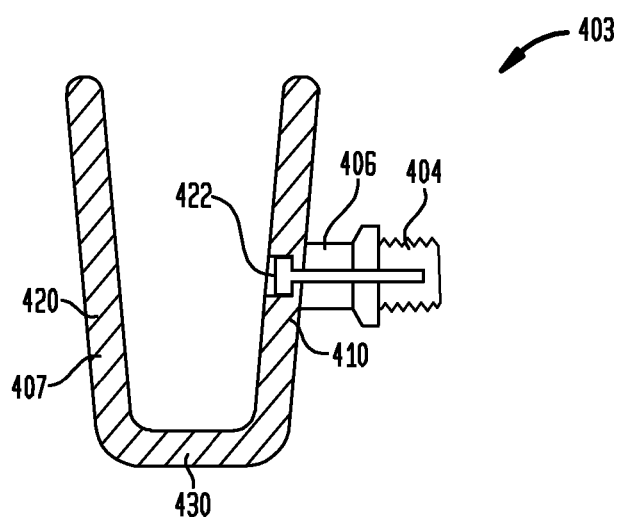
FIG. 4B is a partially cross-sectional view of a variation of the support apparatus of FIG. 4A.

Further by way of example and not by way of limitation, in other embodiments, such as that depicted in FIGS. 4A and 4B, an abutment 406 is connected to a fixture 404. Abutment 406 is, in-turn, connected to the cradle by a screw 422 or other attachment device. In some embodiments, the abutment 406 is integral with cradle 407, while in other embodiments, it is separate from cradle 407. An exemplary embodiment utilizes an abutment having the functionality and/or associated characteristics, including structure and configuration, as the abutment described in U.S. Pat. No. 4,498,461 and/or U.S. Patent Application Publication No. 2009/0082817, the contents of these documents being incorporated by reference herein for application to configuring an abutment for use with the cradle to practice various embodiments of the system. In some embodiments, screw 422 or other attachment device attached to the abutment 406 is proud of an interior surface of cradle 407, or is flush or below the surface of the interior surface of the cradle 407, as is depicted in FIG. 4B.

In embodiments of the present invention, the abutment may be customized to the recipient. In order to improve tissue integration, the surfaces of the implanted abutment (and/or the other components of the implanted cradle) may be modified using any known technology, such as blasting the fixture/other components, surface coating (e.g. silicone coating) of the abutment and/or the cradle 407 and/or the other components. In an embodiment, the configuration of the abutment may vary depending on the anatomy of the recipient. Additionally, any device, system or method which will permit the cradle to be anchored or otherwise attached to the recipient's skull to permit bone conduction hearing assistance may be used in some embodiments.

A cradle in accordance with embodiments of the present invention, such as cradle 407 shown in FIG. 4A, comprise spaced and opposing plates 410 and 420. Opposing plates 410 and 420 are connected by a bridge member 430 and, in these embodiments, form a general U-shape. Also as shown, plate 410 is configured to be attached to fixture 404 and/or abutment 406. Plates 410 and 420 are configured to receive bone conduction device 100 there between and retain bone conduction device 100 against skin 320 proximate to fixture 404.

In certain embodiments, plate 420 is at least partially biased (e.g., biased towards plate 410) so as to exert a compression force on bone conduction device 100.

As noted, bone conduction device 100 rests within the interior of the u-shape of a cradle, such as cradles 307 and 407. In certain embodiments, because the exterior component is a BTE unit, there is little or no need for a holding force specifically to maintain bone conduction device 100 in place, because the BTE unit may rest on the ear. However, as noted, certain embodiments plates 410 and 420 excerpt a compression force on bone conduction device 100.

In specific embodiments, with the exception of the force useful for adequate vibration transfer from bone conduction device 100 through the skin and ultimately to the skull, bone conduction device 100 is held in place with little or no "holding force" applied by the cradle 407 to bone conduction device 100. In this regard, in some embodiments utilizing bone conduction device 100 disclosed herein, the force that is needed in a traditional transcutaneous device that utilizes a magnet to hold the unit containing the external vibrator (e.g., bone conduction device) against the skin (which may be more than, or in addition to, a baseline force needed for adequate vibration transmission through the skin) is not needed.

Regarding the force for adequate vibration transmission, in an embodiment, vibrations representative of received sound are produced by bone conduction device 100. The vibrations representative of received sound are transmitted through the outer skin layer and ultimately to the skull (for conduction to the cochlea). In an embodiment, the cradle applies a force through the skin to bone conduction device 100 that is adequate to permit the vibrations representative of received sound to be transmitted through the outer skin layer and to the cradle and then ultimately to the skull to permit bone conduction hearing assistance to take place. In this regard, referring to FIG. 4A, in an embodiment, bone conduction device 100 acts as a wedge inserted into the concave portion of the u-shape formed by cradle 407, where there is a slight interference between the skin overlaying the concave portion of the u-shape and bone conduction device 100, this interference creating a force that is applied to bone conduction device 100.

In some embodiments, the force for adequate vibration transmission may fall within a range of forces, bounded, on the high end, by the force that would induce discomfort/pain and/or skin necrosis, based on a given configuration of bone conduction device 100 and the support apparatus 403 and/or the physiological features of the recipient. In some embodiments, the force falls within a range of about 2N to about 10N, although in other embodiments, forces outside of this range may be utilized (e.g., a force below 2N may be utilized). Any force applied to bone conduction device 100 to permit bone conduction hearing assistance to be implemented while avoiding and/or limiting unacceptable pain and/or unacceptable necrosis (or the potential for unacceptable necrosis) may be used in some embodiments. In some embodiments, this force/range of forces will be a function of unique physiological characteristics of an individual recipient. Accordingly, in an embodiment, support apparatus 403 and/or bone conduction device 100 may be customized (structurally, locationally, etc.) to fall within the acceptable range of forces.

In some embodiments, the acceptable range of force will be a function of the pressure applied by the support apparatus 403 through the skin to bone conduction device 100 (or visa-versa). Alternatively, there is an acceptable range of pressure that may be experienced by the skin. In this regard, with reference to FIG. 4A by way of example, increasing the area of the cradle 407 that interfaces, through the outer skin layer 320, with the bone conduction device 100, will have an impact on the just-described force range and/or permit a given force to be distributed over a larger area, thus reducing necrosis. Accordingly, in an embodiment, the local contours of the cradle 407 may be modified to better follow the contours of the skin 320 covering cradle 407 and/or to follow the outer dimensions of bone conduction device 100 to adjust the area of the cradle 407 that interfaces, through the outer skin layer 320, with bone conduction device 100.

As previously noted, in certain embodiments utilizing the U-shaped cradle 407, a force of 2-5N applied to bone conduction device 100 is expected to be adequate to permit adequate vibrational transfer from bone conduction device 100 into the skin 320, although forces below and/or above this range may also be used in some embodiments. This force can be evenly distributed over the interfacing surfaces of the cradle 407. In one embodiment, the interfacing area of the cradle 407 is about 2 cm$^2$. In an embodiment, a silicone adhesive could be used to keep a tight fit between bone conduction device 100 and the skin adjacent the skull. Additionally, bone conduction device 100 could be customized to more comfortably fit the recipient.

In an embodiment, the cradle 407 is positioned such that, after implantation into the recipient, a relatively thin layer of skin (about 1 mm in thickness measured normal from the respective local surface of the cradle 407) is located between the cradle 407 and the outside of the recipient (the outside of the skin). This is in contrast to between 2-5 mm and even as much as 10 mm of skin thickness that is present in conventional non-implanted bone conduction systems. In some embodiments, the layer of skin is relatively thin over substantially the entire surface area of the cradle 407, while in other embodiments, the thin layer of skin is located only at and/or adjacent those portions of the cradle 407 that interface, through the skin, with bone conduction device 100. This is especially the case in the area above the outer ear (as compared to, say the skin where conventional bone conduction system vibratory implants are located). In an embodiment, because the layer of skin adjacent to the cradle 407 is thin, in some or all places (and/or, at lest in the places through which the vibrations must travel to reach the support apparatus 403), energy lost by the vibrations generated by bone conduction device 100 between bone conduction device 100 and the cochlea due to, for example, a dampening effect of the skin, is lower than what would be the case if the skin was thicker.

In an embodiment, the bone fixture is placed just above the ear canal as close as possible to the ear canal. In prior bone conduction systems, such as that disclosed in U.S. Pat. No. 4,498,461 and/or the Baha® bone anchored hearing aid, marketed by Cochlear Bone Anchored Solutions AB (previously Entific Medical Systems AB) in Goteborg, Sweden, the implant is often placed about 55 mm posterior to the ear canal. In some embodiments, placing the fixture and/or the rest of the cradle in the area of the skull and soft tissue which is just above the junction where the upper part of the outer ear meets the skull permits the bone conduction device to be used, and also permits the implant (e.g., the bone fixture) to be closer to the cochlea compared to the just-mentioned Baha hearing aid which is placed in the mastoid bone. By placing the bone fixture and/or other components that convey vibrations to the skull closer than 55 mm to the ear canal/to the cochlea, energy loss of the vibrations generated by bone conduction device 100 between bone conduction device 100 and the cochlea is lower than what would be the case if the pertinent components were located about 55 mm from the ear canal/from the cochlea. For example, the energy loss could be as much as 5-15 dB less than the energy loss of components located about 55 mm from the ear canal/cochlea. (About 2 dB of energy is lost for each cm away from the ear canal.) By placing fixture 404 and/or other vibration conducting components closer to the ear canal/by directing vibrations to a portion of the skull closer to the inner ear, less initial vibrational energy is needed for adequate hearing assistance because less energy will be lost. Alternatively, more vibrational energy will reach the cochlea because less energy will be lost, thus improving the quality of the hearing assistance. Indeed, in an embodiment, in holistic terms, what is lost due to transmission of the vibrations through the skin to the skull is compensated for by the closeness to the ear canal of the area where vibrations are applied to the skull. Thus, in an embodiment, the energy loss is comparable to, if not less than, that which is seen in a percutaneous bone conduction system (where there is no need to conduct vibrations through the skin, as the vibrations are conducted directly from the vibrator to the skull by the fixture/fixture-abutment assembly, but the vibrations must travel further thorough the skull to the cochlea).

Referring to FIG. 4A, in an embodiment, forces having a pushing component and a pulling component are conveyed to the skull 305. That is, in an embodiment, bone conduction device 100, by outputting vibrations into the skin 320, pushes itself away from the surface of the skin proximate the location where the vibration is outputted. By way of example and not by way of limitation, with respect to FIG. 4A, when the vibration outputted by bone conduction device 100 pushes bone conduction device 100 to the left away from the right leg of the U-shape of the cradle 407 (and thus away from skull 305), the opposite leg (the left leg) of the U-shape of the cradle 407 reacts against this movement, and thus a "pulling" force is imparted onto the cradle 407 in addition to the "pushing" force imparted onto the right leg of the U-shape. Hence, the cradle 407 receives a pushing force and a pulling force. Thus, the skull 305 receives a pushing force and a pulling force when the skull receives vibrations generated by bone conduction device 100. In an embodiment having a pushing component and a pulling component to the forces applied to the skull 305, functional characteristics of a percutaneous bone conduction system, where an exterior vibrator is directly coupled to the skull may be obtained in a transcutaneous bone conduction system. In an embodiment, the pushing force is equal to or at least about equal to the pulling force.

In contrast, a conventional magnet-held transcutaneous bone conduction system where the bone conduction device is external to the skin only imparts a force that has a "pushing" component and/or to the extent it has a "pulling" component, that component is relatively weak/negligibly impacts the performance of the bone conduction system. Thus, in an embodiment, characteristics of a transcutaneous bone conduction system where the vibrations originate externally to the skin (e.g., lack of skin penetration, and thus lower likelihood of infection) may be combined with characteristics of a percutaneous bone conduction system where the external vibrator is directly coupled to the skull (e.g. push and pull components of the force generated by the vibrator).

In an embodiment, referring to FIG. 4A, the vibrations generated by bone conduction device 100 with a vibrator are transferred through the skin 320 to the cradle 407, and from the cradle to the abutment 406 and then to the fixture 404 and then into the bone 305. In an embodiment, vibrations may be transmitted to the abutment 406 and/or the fixture 404 such that a force is applied to the abutment 406 and/or the fixture 404 at an oblique angle. In an exemplary embodiment, the force applied at an oblique angle to the abutment 406 and/or the fixture 404 may impart both a vertical component (relative to the longitudinal axis of the components) and a horizontal component (normal to the longitudinal axis of the abutment 406 and/or the fixture 404/normal to the outer layer of the skull 305 at the location where the fixture 404 attaches to the skull 305), onto the abutment 406 and/or the fixture 404, thus imparting a moment onto the abutment 406 and/or the fixture 404 and thus onto a portion of the skull 305, in addition to the other forces which may be present.

In summary, certain embodiments are generally directed to a transcutaneous bone conduction system that (i) requires little to no force to hold in place the exterior bone conductor device (the exterior unit that creates the vibration) against the skin covering the skull, (ii) limits audiological performance degradation resulting from transferring vibrations through the skin by permitting vibrations to be sent through the skin and ultimately to the cochlea at a location where the skin is relatively thin relative to other bone conduction systems, (iii) enhances audiological performance vis-à-vis energy loss due to vibrations travelling through the skull, relative to other bone conduction systems, because vibrations are introduced into the skull at a location closer to the ear canal, and (iv) provides a push-pull component of the force applied to the skull, as opposed to only a push component found in other transcutaneous bone conductors where the vibrator is held on the exterior of the skin covering the skull (e.g., with a magnet).

Accordingly, an embodiment provides a transcutaneous bone conduction system in which an external vibrator is held against the skin covering the skull without causing unacceptable discomfort and other disadvantages associated with passive transcutaneous bone conduction systems while providing advantages of a percutaneous bone conduction system.

Also in summary, in some embodiments, there are several features that cause less skin necrosis problems compared to prior transcutaneous bone conduction systems having the bone conduction device (the external component with the vibrator) held in place by magnets. For example, there is little or no pressure force that is needed to hold the external unit in place because it rests on the ear. Still further by example, because the legs of the U-shape of the cradle 407 are relatively close together, the transmission of the vibrations from bone conduction device 100 can be more effective.

In an embodiment, referring to FIG. 5, cradle 507 is perforated. That is, cradle 507 comprises orifices/holes 508 extending from one side of cradle 507 to the other side of cradle 507. These small through holes 508 permit acceptable blood supply and acceptable contact between the thin skin of the outer layer of the skin and the underlying soft tissue (especially in the case of, referring to FIG. 4A, an abutment 406 being used to create a stand-off for the cradle 507 relative to the skull 305). In an embodiment, this can reduce the risk of skin necrosis/reduce skin necrosis to an acceptable level. In an embodiment, the perforations allow acceptable blood supply to/from the thin skin and the skin will be provided with a good "connection" to the rest of the soft tissue.

FIGS. 4A and 4B illustrate an embodiment in which the cradle 407 is placed onto an intracutaneous abutment 406 which is connected to the fixture 404 by a conventional abutment screw 422 or the like. The length of the abutment 406 may vary depending on the anatomy of the recipient. As an alternative, the abutment 406 and/or the fixture 404 and/or the cradle 407 might be pre-mounted or integral to form a single unit.

In an embodiment, the implanted components of the support apparatus 403, including the cradle 407, are made of titanium or any other non-magnetic/non-ferrous material or any other material which is MRI compatible but will also permit the embodiments disclosed herein to be practiced. In contrast, a traditional implant (e.g., fixture, abutment, etc.) for a bone conduction system utilized in a transcutaneous bone conduction system is made of metal that is not MRI compatible (e.g., the material is magnetic to permit the exterior vibrator component to adhere to the outside of the skin without piercing the skin). As an MRI uses a powerful magnetic field, some people with hearing aid implants, including bone conduction implants, cannot obtain the benefits of an MRI. (The implant may be heated and/or be pulled/pushed due to the magnetic field.) Because embodiments of the support apparatus 403 utilize material that is MRI compatible, a recipient having a support apparatus 403 implanted in his or her head may still safely and painlessly have his or her head exposed to the MRI magnetic field without fear of pain or damage and/or without the support apparatus 403 causing a significant "blank spot" (due to interference with the magnetic field by the implant) in the image obtained by the MRI.

In an embodiment, acoustic neuroma recipients having an implanted support apparatus 403 anchored to their skull may safely and effectively have MRIs taken of their head. In an embodiment, there is a method of removing an acoustic neuroma tumor in a recipient, which induces one-sided deafness in the recipient. Hearing is at least partially restored by implanting a support apparatus according to an embodiment disclosed herein. The recipient receives yearly MRI checkups with the implant implanted in the recipient's head to check to see if the tumor has returned.

In the embodiments depicted in FIGS. 2-5 and 7A-7C, the cradle has a "U-shaped cross-section. Referring to FIG. 5, the cradle 507 has a first plate 510 and a second opposing plate 520. The plates are separated by a bridge member as described with reference to FIGS. 4A and 4B. In embodiments of the present invention, plate 510, which is placed against the skull/located closer to the skull, is configured to be attached to a fixture implanted in the skull. Additionally, plate 510 has a greater surface area than plate 520, which is placed inside the outer ear. The greater surface area reduces the pressure applied by the skin that is used to hold bone conduction device 100 against the skin so as to adequately transfer vibrations into the skin. A reduction in pressure reduces the effects of necrosis.

In certain embodiments, plate 520 may have a larger surface area than that depicted in the FIGs. (relative to the surface area of plate 510), thus reducing the pressure applied through the skin on the other side of bone conduction device 100 in a similar manner as described above. Additionally, in an embodiment, plate 510 attached to the skull may have a smaller surface area than that depicted in the FIGs. (relative to the surface area of the leg 520).

In embodiments, plates 510 and 520 of cradle 507 are thin perforated pressure plates. The thinness of the plates also aids in reducing the risk of skin necrosis.

The embodiments have so far been described with reference to U-shaped cradles. In an alternative embodiment such as that depicted in FIG. 6, the cradle 607 of the support apparatus 624 may have a J-shape to allow, relative to the skull of the recipient when the recipient is sitting or standing upright), a parallel vibration mode. In this embodiment, the J-shaped fixture may permit bone conduction device 100 to be rotated (albeit, in some embodiments, slightly) between the skin adjacent the longer plate of the J-shape and the skin adjacent the side of the skull opposite the long plate of the J-shape. This rotation permits vibrations to be transferred into the skin in a different manner than the "push-pull" manner described above.

FIG. 6 depicts a J-shaped cradle 607. In an embodiment, the short plate of the J-shape has a clearance for a surgical wrench to permit attachment of the cradle 607 to the fixture 604 and/or an abutment and/or to permit the fixture 604 to be screwed into the skull 305.

In an embodiment, the outer ear 102 may act as a spring and can thus be used to press bone conduction device 100 to the implanted pressure plate 510 with appropriate force. However, in such embodiments, it may be useful to customize bone conduction device 100 to the recipient and/or customize other components (e.g., the cradle) to the recipient. In an embodiment, referring to FIG. 5, the cradle 507 may be used as a spring. Specifically, in the case of the U-shaped cradle 507, one plate 520 functions as a spring and is located under the skin of the outer ear. Spring plate 520 will press the bone conduction device with appropriate force against the skin above the implanted leg 510 opposite leg 520.

In an embodiment, the implantable parts may be used in combination/be combined with bone conduction eyeglasses. That is, in an embodiment, a pair of eyeglasses forms the bone conduction device, where the vibrator may be installed in a pair of eyeglasses, and the support apparatus may be used to receive the vibrations generated by the eyeglasses.

In an embodiment, because there is no skin penetration of any component of the support apparatus (the support apparatus is fully implantable), the potential for skin infections associated with percutaneous implants are reduced and/or eliminated. Further, the need for frequent (sometimes daily) maintenance of the skin proximate the implant, as is associated with a percutaneous implant, is also vitiated by an embodiment of the support apparatus. Furthermore, the totally implanted support apparatus provides superior aesthetics to a percutaneous implant. This is especially the case when the support apparatus is custom fitted to the body of a recipient.

Figure 7A:
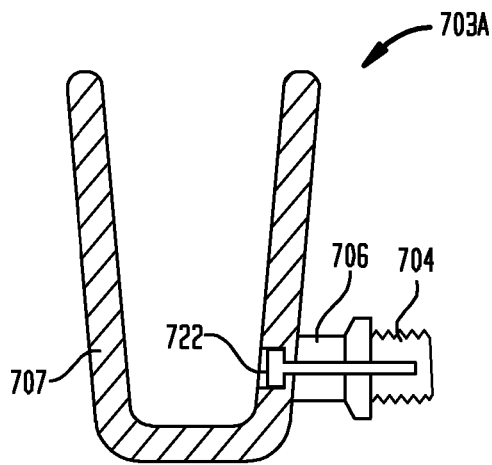
FIG. 7A is a partially cross-sectional view of an implantable support apparatus in accordance with embodiments of the present invention.
Figure 7B:
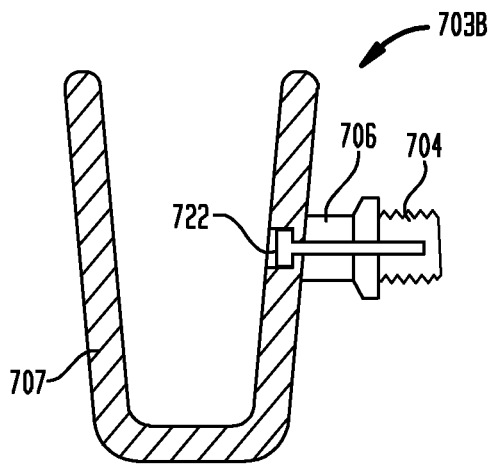
FIG. 7B is a partially cross-sectional view of an implantable support apparatus in accordance with embodiments of the present invention.
Figure 7C:
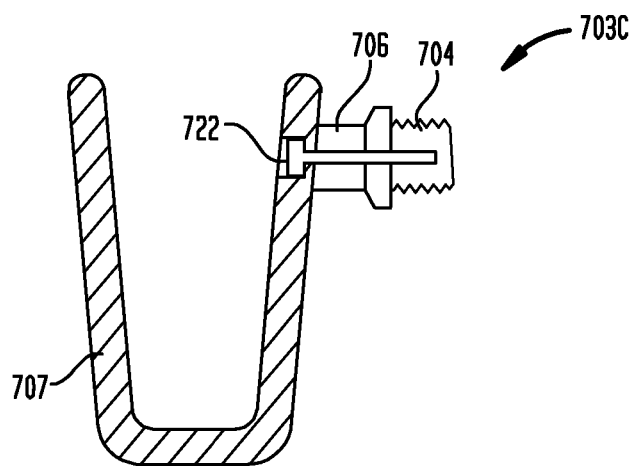
FIG. 7C is a partially cross-sectional view of an implantable support apparatus in accordance with embodiments of the present invention.

FIGS. 7A-7C depict alternate embodiments of support apparatus 703A, 703B and 703C, respectively. In each of these embodiments, the fixture 704 and/or the abutment 706 are located at different locations on the cradle 707. Additionally, the abutment screw 722 is countersunk below the exterior surface of the cradle 707 so that bone conduction device 100 will not interface, through the skin, with the abutment screw 722.

As detailed above, embodiments of the present invention are generally described with reference to bone conduction devices and systems comprising a BTE unit. It would be appreciated that embodiments of the present invention may also be implemented with other BTE units which are not a bone conduction device.

As noted above, this patent application claims foreign priority to German Patent Application No. 102009014772.4, entitled "Hearing Aid Device," filed on 25 Mar. 2009, the entire contents of which are incorporated by reference herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A transcutaneous bone conduction system, comprising:
   a bone conduction device configured to vibrate in response to received sound, the bone conduction device external to a totally implantable support apparatus positionable under a recipient's skin, the totally implantable support apparatus comprising:
  a fixture configured to be implanted in the skull; and
  a substantially rigid cradle having first and second opposing, spaced plates connected by a bridge member, wherein the first plate is configured to be secured to the fixture and wherein the space between the plates is sufficient to receive the bone conduction device, and wherein the plates are configured to retain the bone conduction device against the skin proximate to the first plate.

2. The system of claim 1, wherein the second plate is at least partially biased towards the first plate to retain the bone conduction device against the recipient's skin.

3. The system of claim 1, wherein the surface area of the first of the first plate is substantially larger than the surface area of the second plate.

4. The system of claim 1, wherein the first plate, second plate and bridge member collectively form a U-shape.

5. The system of claim 1, wherein the first plate, second plate and bridge member collectively form a J-shape.

6. The system of claim 1, wherein the first plate is configured to be positioned adjacent a region of the recipient's skull, and wherein the second plate is configured to be positioned in the recipient's outer ear.

7. The system of claim 6, wherein a portion of the bridge member extends underneath the skin connecting the skin of the outer ear to the skin adjacent the skull.

8. The system of claim 1, wherein the totally implantable apparatus is substantially free of ferrous and magnetic material.

9. The system of claim 1, wherein the first and second plates are configured to compress the bone conduction device there between, and wherein a compressive force on the bone conduction device is approximately 2N to approximately 10N when about 1 mm of the recipient's skin is located between each of the respective plates and the bone conduction device.

10. The system of claim 1, further comprising a subcutaneously positioned abutment adjacent the fixture, wherein the vibration of the bone conduction device applies a force to the abutment.

11. The system of claim 1, wherein the totally implantable support apparatus comprises titanium.

12. The system of claim 1, wherein the first plate is contoured to match the surface of a region of the recipient's skull.

13. The system of claim 1, wherein one or more of the first plate, second plate and bridge member are perforated.

14. A support apparatus positionable under a recipient's skin configured for use with an external bone conduction device that vibrates in response to received sound, the apparatus comprising:
  a fixture configured to be implanted in the skull; and
  a substantially rigid cradle having opposing, spaced plates connected by a bridge member, wherein a first of the plates is configured to be secured to the fixture and wherein the space between the plates is sufficient to receive the bone conduction device, and wherein the plates are configured to retain the bone conduction device against the skin proximate to the first plate.

15. The apparatus of claim 14, wherein the second plate is at least partially biased towards the first plate to retain the bone conduction device against the recipient's skin.

16. The apparatus of claim 14, wherein the surface area of the first of the first plate is substantially larger than the surface area of the second plate.

17. The apparatus of claim 14, wherein the first plate, second plate and bridge member collectively form a U-shape.

18. The apparatus of claim 14, wherein the first plate, second plate and bridge member collectively form a J-shape.

19. The apparatus of claim 14, wherein the first plate is configured to be positioned adjacent a region of the recipient's skull, and wherein the second plate is configured to be positioned in the recipient's outer ear.

20. The apparatus of claim 19, wherein a portion of the bridge member extends underneath the skin connecting the skin of the outer ear to the skin adjacent the skull.

21. The apparatus of claim 14, wherein the totally implantable apparatus is substantially free of ferrous and magnetic material.

22. The apparatus of claim 14, wherein the first and second plates are configured to compress the bone conduction device there between, and wherein a compressive force on the bone conduction device is approximately 2N to approximately 10N when about 1 mm of the recipient's skin is located between each of the respective plates and the bone conduction device.

23. The apparatus of claim 14, further comprising a subcutaneously positioned abutment adjacent the fixture, wherein the vibration of the bone conduction device applies a force to the abutment.

24. The apparatus of claim 14, wherein the first plate is contoured to match the surface of a region of the recipient's skull.

25. The apparatus of claim 14, wherein one or more of the first plate, second plate and bridge member are perforated.

26. The apparatus of claim 1, wherein the bone conduction device is configured to be placed against outer skin of the recipient.

27. The apparatus of claim 14, wherein the external bone conduction device is configured to be placed against outer skin of the recipient.

28. The transcutaneous bone conduction system of claim 1, wherein the bone conduction device is a Behind-The-Ear (BTE) bone conduction device, wherein the (BTE) bone conduction device is configured to be positioned behind an ear of the recipient.

29. The apparatus of claim 14, wherein the external bone conduction device is a Behind-The-Ear (BTE) bone conduction device, the BTE bone conduction device being configured to be positioned behind an ear of the recipient, the BTE bone conduction device being further configured to be positioned within the cradle.

* * * * *